United States Patent [19]

Bruijnjé et al.

[11] Patent Number: 5,047,256

[45] Date of Patent: Sep. 10, 1991

[54] FLAVORING WITH ALKYL (3-METHYLTHIO)-BUTYRATES

[75] Inventors: Arnold Bruijnjé; Theo Heideman, both of Huizen; Hans J. Wille, Bussum, all of Netherlands

[73] Assignee: Naarden International N.V., Huizerstraatweg, Netherlands

[21] Appl. No.: 595,704

[22] Filed: Oct. 9, 1990

Related U.S. Application Data

[63] Continuation of Ser. No. 310,953, Feb. 15, 1989, abandoned.

[30] Foreign Application Priority Data

Feb. 26, 1988 [NL] Netherlands ............... 8800502

[51] Int. Cl.$^5$ ............................................. A23L 1/235
[52] U.S. Cl. ..................................... 426/535; 560/152
[58] Field of Search ................... 560/152; 426/535

[56] References Cited

U.S. PATENT DOCUMENTS 4,426,403 1/1984 Cyronak et al. ............... 560/152 X
4,631,194 12/1986 Courtney et al. ............... 560/152 X
4,739,105 4/1988 Courtney et al. ................. 560/152

FOREIGN PATENT DOCUMENTS 891391 8/1953 Fed. Rep. of Germany .

*Primary Examiner*—Joseph Golian
*Attorney, Agent, or Firm*—Cushman, Darby & Cushman

[57] ABSTRACT

The invention relates to alkyl (3-methylthio)-butyrates wherein the alkyl group has 4 to 5 carbon atoms, to their use in flavor compositions and to the use of these compounds or flavor composition comprising these compounds in foodstuffs and stimulants. The compounds impart a fresh fruit flavor character. Preferred is isobutyl (3-methylthio)-butyrate.

7 Claims, 1 Drawing Sheet

1
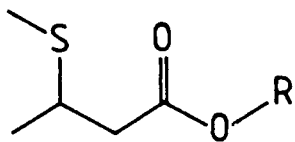
2
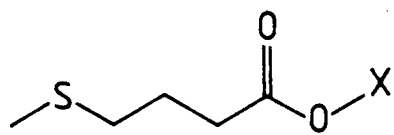
3
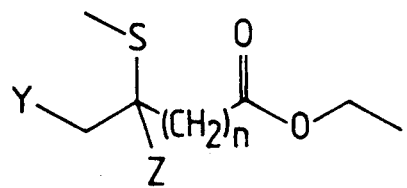
4
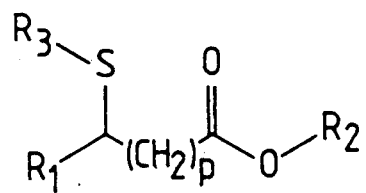
5
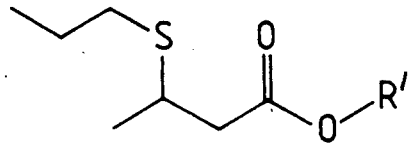

FLAVORING WITH ALKYL (3-METHYLTHIO)-BUTYRATES

This is a continuation of application Ser. No. 07/310,953, filed on Feb. 15, 1989, which was abandoned upon the filing hereof.

The invention relates to alkyl (3-methylthio)-butyrates, to compositions containing one or more of these compounds as flavour component, as well as to one or more of these compounds or foodstuffs and stimulants flavoured with said compositions.

There is a continuing interest in the preparation of synthetic flavour components and the use thereof in foodstuffs and stimulants. On the one hand, this interest is stimulated by the insufficient amount and often varying quality of natural flavour complexes such as extracts, ethereal oils, concentrates etc. On the other hand, the usual industrial methods of preparing foodstuffs often have a negative influence on the organoleptic quality of such flavour complexes, as a result of which they no longer serve their purpose: improving or complementing the flavour of the foodstuffs to which they have been added. It is a common problem with the industrial preparation of foodstuffs that therewith the flavour mostly loses the fresh character and acquires a clear cooked or conserved note. This problem can only be very partly solved with the current synthetic flavour components. There is therefore urgent need of flavour components which are capable of imparting a fresh character to the flavour of foodstuffs and stimulants. This applies in particular to fruit conserves and to other foodstuffs and stimulants which have a fruit flavour.

Surprisingly, it has now been found that alkyl (3-methylthio)-butyrates having the formula:

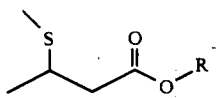

(1)

in which R is an alkyl group having 4 or 5 carbon atoms, are valuable flavour components which can impart a flavour character of fresh fruit to foodstuffs and stimulants or can improve or strengthen such a character.

Many esters of (alkylthio)-alkanecarboxylic acids are known, as well as the use thereof, as flavour component in foodstuffs. Thus, (4-methylthio)-butyrates having formula 2:

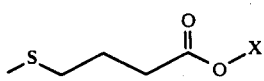

(2)

in which X is a methyl or ethyl group, are known from Dutch patent application 7314726, laid open to public inspection, and the corresponding U.S. Pat. specifications Nos. 3,870,800 and 3,904,556. About these compounds it is stated that they have a sweet, roasted, nut-, dairy- and vegetable-like flavour, and, respectively, a sweet, metallic, fruity, cheese- and onion-like flavour and odour. Nowhere, however, is it mentioned that these compounds would be suitable for imparting a flavour note of fresh fruit to foodstuffs. On the contrary, the sweet fruit-like character of the ethyl ester rather points in the direction of flavour notes of cooked fruit, jam and fruit conserves.

In U.S. Pat. specification No. 4,426,403, ethyl (methylthio)-alkanoates are described which satisfy formula 3:

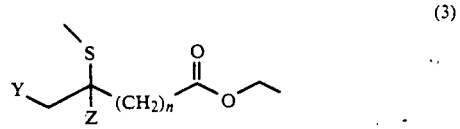

(3)

in which Y and Z are a hydrogen atom or an alkyl group and n has the values 0 or 1. The most important compound of this group is ethyl (2-methylthio)-isobutyrate, which has a flavour resembling that of green pine needles. About ethyl (3-methylthio)-butyrate it is briefly mentioned that it has a pineapple/strawberry flavour, but without any indication that the compound would be suitable for imparting precisely a fresh fruit character to foodstuffs.

In U.S. Pat. specification No. 4,590,082, esters of mercapto- and methylthio-alkanoates are described, which satisfy formula 4:

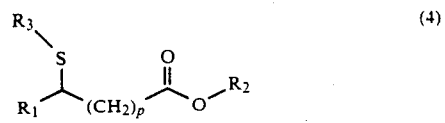

(4)

in which $R_1$ and $R_3$ are a hydrogen atom or a methyl group, $R_2$ is a cycloalkyl group possibly substituted by an alkyl group, and p has the values 0, 1 or 2. About these compounds it is stated that they can improve or strengthen a range of the most divergent flavour notes, but, however, the fresh fruit character is not mentioned among them. Among the many compounds defined in this patent specification there is not a single ester of 3-methylthio-butyric acid. About some of the compounds that are mentioned by name it is stated that they have, inter alia, also a fruit-, kiwi-, pineapple- or citrus-like flavour note, but without any mention, however, of the so greatly valued fresh fruit character.

In U.S. Pat. specification No. 4,631,194 there are described, inter alia, esters of 3-propylthio-butyric acid which satisfy formula 5:

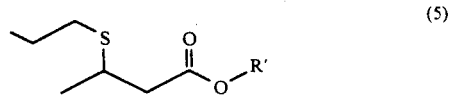

(5)

in which R' is an alkyl group having 1-4 carbon atoms or an alkenyl group having 3-6 carbon atoms. The specifically mentioned methyl and ethyl ester have a fresh green, onion-like, fruit-like-, dried litchi- or garlic-like flavour, but are especially suitable for foodstuffs having a durian, onion or garlic flavour. In the case of the also specifically mentioned isobutyl-and the 3-hexenyl ester, every indication of a fresh and/or fruit-like flavour is missing. The obvious conclusion is that the low alkyl esters of this acid still have a somewhat fresh and/or fruity flavour note but that this is totally absent with alkyl or alkenyl esters having 4 or more carbon atoms.

In U.S. Pat. specification No. 4,594,254, cis-3-hexenyl and citronellyl (4-methylthio)-butyrate are described.

The latter has a fresh lemon- and lemon juice-like, floral and grapefruit-like flavour and is suitable for addition to foodstuffs having the flavour of tropical fruits.

In U.S. Pat. specification No. 4,634,595, esters of mercapto- and methylthio-alkanoates are described which also satisfy formula 4, in which $R_1$ and $R_3$ are a hydrogen or a methyl group, $R_2$ is now, however, a phenylalkyl group, and p has the values 0, 1 or 2. About these compounds too it is stated that they can improve or strengthen a range of the most divergent flavour notes, but the fresh fruit character is, however, not mentioned among them. Among the many compounds mentioned specifically in this patent specification there is not a single ester of 3-methylthio-butyric acid. None of the specifically mentioned compounds has a fruit flavour or is apparently suitable for flavouring foodstuffs having a fruit flavour.

BRIEF DESCRIPTION OF THE DRAWINGS

FIG. 1 illustrates the compounds of the present invention.

FIG. 2 illustrates compounds known in the art.
FIG. 3 illustrates compounds known in the art.
FIG. 4 illustrates compounds known in the art.
FIG. 5 illustrates compounds known in the art.

The compounds according to the invention, which were not known up to now, are very suitable for imparting a fresh flavour note to foodstuffs and stimulants which have a fruit flavour, or to improve or to strengthen such a note. They are especially capable of imparting to such products a flavour character of fresh red fruits, such as strawberries and raspberries. Preferably, isobutyl (3-methylthio)-butyrate is used for this.

The esters according to the invention can be prepared in a manner customary for such compounds, for example by addition of methylmercaptan to the corresponding alkylcrotonates.

The compounds according to the invention can be added as such to foodstuffs and stimulants, or they can first be mixed with the carriers or solvents usual in the flavour industry. Preferably, however, they are incorporated in flavour compositions. By the expression "flavour composition" is meant a mixture of flavour components of natural and/or synthetic origin, if desired dissolved in a suitable solvent or mixed with a powdered substrate, or processed into a powdered product, that is used in order to impart a desired flavour to all kinds of foodstuffs and stimulants. By "foodstuffs and stimulants" are meant: solid or liquid products intended for human consumption, including tobacco products, pharmaceuticals and toothpaste.

Flavour components of natural or synthetic origin which can be combined, in flavour compositions, with the compounds according to the invention, are mentioned for example in S. Arctander, Perfume and Flavor Chemicals (Montclair, N.J., 1969), in S. Arctander, Perfume and Flavor Materials of Natural Origin (Elizabeth, N.J., 1960), in T.E. Furia et al., CRC Fenaroli's Handbook of Flavor Ingredients, 2nd ed. (Cleveland, CRC Press Inc., 1975) and in H.B. Heath, Source Book of Flavors, (The AVI Publishing Company Inc., Westport, Conn., 1981).

The amounts in which the compounds according to the invention can be used in flavour compositions or products to be flavoured can vary within wide limits and depend, among other things, on the nature of the product in which the compounds are used, on the nature and the amount of the other flavour components in the flavour composition and on the flavour effect aimed at. Therefore it is only possible to indicate very global limits, with which, however, the expert is provided with sufficient information to use the compounds according to the invention self-reliantly. In many cases an amount of only 0.1 parts per million by weight (0.1 ppm) of the compound according to the invention in a flavour composition will already be sufficient for obtaining a clearly observable effect. On the other hand, in order to obtain special flavour effects, it is possible to use amounts of even 1000 parts per million by weight or more in a composition. In products flavoured with the aid of flavour compositions these concentrations are proportionally lower, depending on the amount of composition used in the product.

The following examples serve only to illustrate the preparation and use of the compounds according to the invention. Nevertheless, the invention is not limited thereto.

EXAMPLE I

Preparation of isobutyl (3-methylthio)-butyrate 0.3 g of a 30% solution of sodium methoxide in methanol was added to 142 g (1 mol) isobutylcrotonate, cooled to about 10° C. In two hours, 48 g (1 mol) methylmercaptan was passed into this mixture via a gas inlet tube, the temperature of the reaction mixture being kept at about 5° C. Then the reaction mixture was distilled under reduced pressure. 167 g of the desired ester was obtained; yield: 88%; boiling point: 74° C. / 0.13 kPa; NMR (100 Mhz, dissolved in $CCl_4$, δ in ppm relative to TMS): 0.94 (6H,d,J=7Hz), 1.30 (3H,d,J=7Hz), 1.92 (1H,m,J=7Hz), 2.06 (3H,s), 2.48 (2H,m), 3.04 (1H,m), 3.82 (2H,d,J=7Hz).

EXAMPLE II

A strawberry flavour composition was prepared according to the following recipe:

|  | parts by weight |
|---|---|
| Amyl butyrate | 0.2 |
| Ethyl capronate | 0.5 |
| δ-Decalactone | 0.5 |
| Ethyl valerianate | 0.6 |
| 3-Hexenyl-1 acetate | 0.5 |
| Ethyl 2-methylbutyrate | 1.0 |
| 2-Methylbutyric acid | 1.0 |
| 3-Hexenol-1 | 1.0 |
| Ethyl butyrate | 2.2 |
| 2,5-Dimethyl-4-hydroxy-2H-furan-3-one | 10.0 |
| Ethanol | 982.5 |
| Total | 1000.0 |

A second strawberry flavour composition was also prepared according to the above recipe, but to it was also added 0.02 per 1000 parts by weight isobutyl (3-methylthio)-butyrate.

With both compositions, a yoghurt drink having a strawberry flavour was prepared by in each case adding 80 g sugar and 1 g of one of both flavour compositions to 1 kg natural drinking yoghurt. Both yoghurt drinks were evaluated by a panel of 5 persons who, although experienced, were not especially trained for this experiment. They all preferred the yoghurt drink flavoured with the second composition because this had a much fresher and juicier strawberry flavour than the other yoghurt drink, the flavour of which was more reminiscent of strawberry jam.

We claim:

1. Flavor composition having a fresh red fruit flavor character which comprises an alkyl (3-methylthio)-butyrate having the formula:

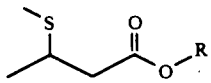

in which R is an alkyl group having 4 or 5 carbon atoms.

2. Flavor composition according to claim 1, which comprises 0.1–1000 ppm of said alkyl (3-methylthio)-butyrate.

3. Flavor composition according to claim 1, wherein said alkyl (3-methylthio)-butyrate is isobutyl (3-methylthio)-butyrate.

4. Flavored product having a fresh red fruit flavor character which comprises an alkyl (3-methylthio)-butyrate having the formula:

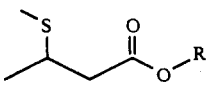

in which R is an alkyl group having 4 to 5 carbon atoms.

5. Flavored product according to claim 4, wherein said alkyl (3-methylthio)-butyrate is isobutyl (3-methylthio)-butyrate.

6. Process for imparting a fresh red fruit flavor character to foodstuffs and stimulants which comprises adding an alkyl (3-methylthio)-butyrate having he formula:

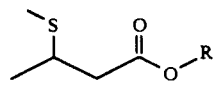

in which R is an alkyl group having 4 to 5 carbon atoms.

7. Process for imparting a fresh fruit flavor to foodstuffs and stimulants which comprises adding a flavor composition according to claim 1.

* * * * *